(12) United States Patent
Heikenfeld

(10) Patent No.: US 12,429,482 B2
(45) Date of Patent: Sep. 30, 2025

(54) APTAMER SENSORS WITH REFERENCE AND COUNTER VOLTAGE CONTROL

(71) Applicant: University of Cincinnati, Cincinnati, OH (US)

(72) Inventor: Jason Heikenfeld, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 342 days.

(21) Appl. No.: 18/246,207

(22) PCT Filed: Sep. 24, 2021

(86) PCT No.: PCT/US2021/051972
§ 371 (c)(1),
(2) Date: Mar. 22, 2023

(87) PCT Pub. No.: WO2022/067051
PCT Pub. Date: Mar. 31, 2022

(65) Prior Publication Data
US 2023/0358738 A1    Nov. 9, 2023

Related U.S. Application Data

(60) Provisional application No. 63/215,605, filed on Jun. 28, 2021, provisional application No. 63/197,669, (Continued)

(51) Int. Cl.
*G01N 27/327* (2006.01)
*G01N 33/53* (2006.01)
*G01N 33/543* (2006.01)

(52) U.S. Cl.
CPC ..... *G01N 33/5438* (2013.01); *G01N 27/3277* (2013.01); *G01N 33/5306* (2013.01)

(58) Field of Classification Search
CPC ........... G01N 27/3277; G01N 33/5306; G01N 33/5308; G01N 33/5438; A61B 5/1451; A61B 5/14546; A61B 5/1468
See application file for complete search history.

(56) References Cited

U.S. PATENT DOCUMENTS 10,182,795 B2    1/2019   Heikenfeld et al.
10,506,968 B2   12/2019   Heikenfeld et al.
(Continued)

OTHER PUBLICATIONS

W. Wang, Electrochemical behavior of arctigenin at a novel voltammetric sensor based on Iodide/SWCNTs composite film modified electrode and its sensitive determination, Journal of Electroanalytical Chemistry, 772, 2016, pp. 17-26 (Year: 2016).*

(Continued)

*Primary Examiner* — C. Sun
(74) *Attorney, Agent, or Firm* — Wood Herron & Evans LLP

(57) ABSTRACT

Devices and methods for measuring an analyte. A sensing device includes a sensor and a detection circuit operatively coupled to the sensor. The sensor includes a working electrode having an aptamer and an attached redox couple to electrochemically measure the analyte. The detection circuit is configured to apply a first scan having a first scan range to the sensor, and determine a position of a redox peak in the first scan. In response to the first scan range not matching the position of the redox peak, the detector circuit defines a second scan range that matches the position of the redox peak, and applies a second scan having the second scan range to the sensor.

20 Claims, 5 Drawing Sheets

Related U.S. Application Data filed on Jun. 7, 2021, provisional application No. 63/150,675, filed on Feb. 18, 2021, provisional application No. 63/083,023, filed on Sep. 24, 2020.

(56) References Cited

U.S. PATENT DOCUMENTS

| | | | |
|---|---|---|---|
| 2016/0166186 A1 | | 6/2016 | Ferguson et al. |
| 2017/0299540 A1* | | 10/2017 | Wu ............... G01N 27/3272 |
| 2018/0113123 A1 | | 4/2018 | Khine et al. |
| 2020/0138347 A1 | | 5/2020 | Heikenfeld |

OTHER PUBLICATIONS

PCT Office, International Search Report and Written Opinion issued in PCT/US2021/051972 dated Dec. 23, 2021.

European Patent Office, Supplementary European Search Report, Application No. 21873524.9, dated Aug. 2, 2024 (9 pages).

Wenjing Wang et al., Electrochemical behavior of arctigenin at a novel voltammetric sensor based on Iodide/SWCNTs composite film modified electrode and its sensitive determination, Journal of Electroanalytical Chemistry, Elsevier, Amsterdam, NL, vol. 772, Apr. 13, 2016, pp. 17-26, XP029537658, Issue 1572-6657, <http://dx.doi.org/10.1016/j.jelechem.2016.04.002> (10 Pages).

Abdolmajid Bayandori Moghaddam et al., Direct electron transfer and biocatalytic activity of iron storage protein molecules immobilized on electrodeposited cobalt oxide nanoparticles, Microchim Acta, an International Journal of Micro and Traceanalysis, Springer-Verlag, VI, vol. 173, No. 3-4, Feb. 19, 2011, pp. 317-322, XP019901131, Issue 1436-5073, DOI: 10.1007/s00604-011-0554-y (6 pages).

Md. Rajabul Akanda et al., Ferritin-Triggered Redox Cycling for Highly Sensitive Electrochemical Immunosensing of Proten, Analytical Chemistry, vol. 90, No. 13, Jul. 3, 2018, pp. 8028-8034, XP093176002, Issue 0003-2700, DOI: 10.1021/acs.analchem. 8b00933 (7 pages).

* cited by examiner

APTAMER SENSORS WITH REFERENCE AND COUNTER VOLTAGE CONTROL

CROSS-REFERENCE TO RELATED APPLICATION

This application claims the benefit of Intl. App. No. PCT/US2021/051972, filed on Sep. 24, 2021 claiming the benefit of U.S. Patent Application Ser. No. 63/083,023, filed on Sep. 24, 2020, U.S. Patent Application Ser. No. 63/150,675, filed on Feb. 18, 2021, U.S. Patent Application Ser. No. 63/197,669, filed on Jun. 7, 2021, and U.S. Patent Application Ser. No. 63/215,605 filed on Jun. 28, 2021. The disclosures of each of the above applications are incorporated by reference herein in their entireties.

BACKGROUND OF THE INVENTION

This section is intended to introduce the reader to various aspects of the art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Aptamers are molecules that bind to a specific target molecule. Electrochemical aptamer sensors include an aptamer sequence that specifically binds to an analyte of interest, and that is attached to an electrode. The aptamer has an attached redox active molecule (redox couple) which can transfer electrical charge to or from the electrode. When an analyte binds to the aptamer, the aptamer changes shape, changing the availability of the redox couple to transfer charge to and from the electrode. This results in a measurable change in electrical current that can be translated into a measure of concentration of the analyte. A major unresolved challenge for aptamers is a lack of simple ways to address drift in the reference potential measurement, and addressing the need for simple ways to obtain a stable and repeatable reference potential measurement.

Thus, a need exists for improved devices and methods that address drift in the reference potential measurements and that provide stable and repeatable reference potential measurements.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention.

Many of the drawbacks and limitations stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sensing technology into proximity with sample fluids containing at least one analyte of interest to be measured.

In an embodiment of the invention, a sensing device for measuring an analyte is provided. The sensing device includes a sensor and a detection circuit operatively coupled to the sensor. The sensor includes a plurality of electrodes having a working electrode, a counter electrode, and a plurality of aptamers with an attached redox couple configured to measure the analyte. The detection circuit is configured to apply a first scan having a first scan range to the sensor, and determine a position of a redox peak in the first scan. In response to the first scan range not matching the position of the redox peak, the detector circuit defines a second scan range that matches the position of the redox peak, and applies a second scan having the second scan range to the sensor.

In an aspect of the invention, the detection circuit may be further configured to determine, based on the second scan, a measured scan voltage at which an electron transfer rate of the redox tag is at a peak value.

In another aspect of the invention, the measured scan voltage may be within 200 mV, 100 mV, 50 mV, 20 mV, 10 mV, 5 mV, or 1 mV of a working electrode voltage at which the electron transfer rate of the redox tag is at the peak value.

In another aspect of the invention, the measured scan voltage may be used to determine the second scan range, and a midpoint voltage of the second scan range may be no more than 200 mV, 100 mV, 50 mV, 20 mV, 10 mV, 5 mV, or 1 mV different than the first scan range.

In another aspect of the invention, at least one of the plurality of electrodes may be configured to be external to a body and in conductance with the working electrode, and the working electrode may be in electrical contact with a biofluid originating in the body.

In another aspect of the invention, the at least one of the plurality of electrodes configured to be external to the body may be the reference electrode.

In another aspect of the invention, the at least one of the plurality of electrodes configured to be external to the body may be the counter electrode.

In another aspect of the invention, a voltage drop at the working electrode may be at least one of >20%, >50%, or >90% of a total applied voltage between the working electrode and the external electrode.

In another aspect of the invention, the plurality of electrodes may further include at least one non-working electrode configured to be applied externally to a body such that the non-working electrode is in conductance with the working electrode when the working electrode is in electrical contact with a biofluid originating in the body.

In another aspect of the invention, the non-working electrode may be the reference electrode.

In another aspect of the invention, the non-working electrode may be the counter electrode.

In another aspect of the invention, the voltage drop at the working electrode may be >20, >50, or >90 of a total applied voltage between the working electrode and the non-working electrode.

In another embodiment of the invention, a method for measuring the analyte with the device comprising the sensor and the detection circuit is provided. The method includes applying the first scan having the first scan range to the sensor, and in response to the first scan range not matching the position of the redox peak, defining the second scan range that matches the position of the redox peak and applying the second scan having the second scan range to the sensor.

In an aspect of the invention, the first scan may be part of a first partial scan that includes one or more portions of a voltage range associated with a full scan.

In another aspect of the invention, the one or more portions of the voltage range associated with full scan may include a baseline scan.

In another aspect of the invention, the method may further include determining, based on the second scan, a measured scan voltage at which an electron transfer rate of the redox tag is at a peak value.

BRIEF DESCRIPTION OF THE DRAWINGS

The objects and advantages of the present invention will be further appreciated in light of the following detailed descriptions and drawings in which.

DEFINITIONS

Figure 1:
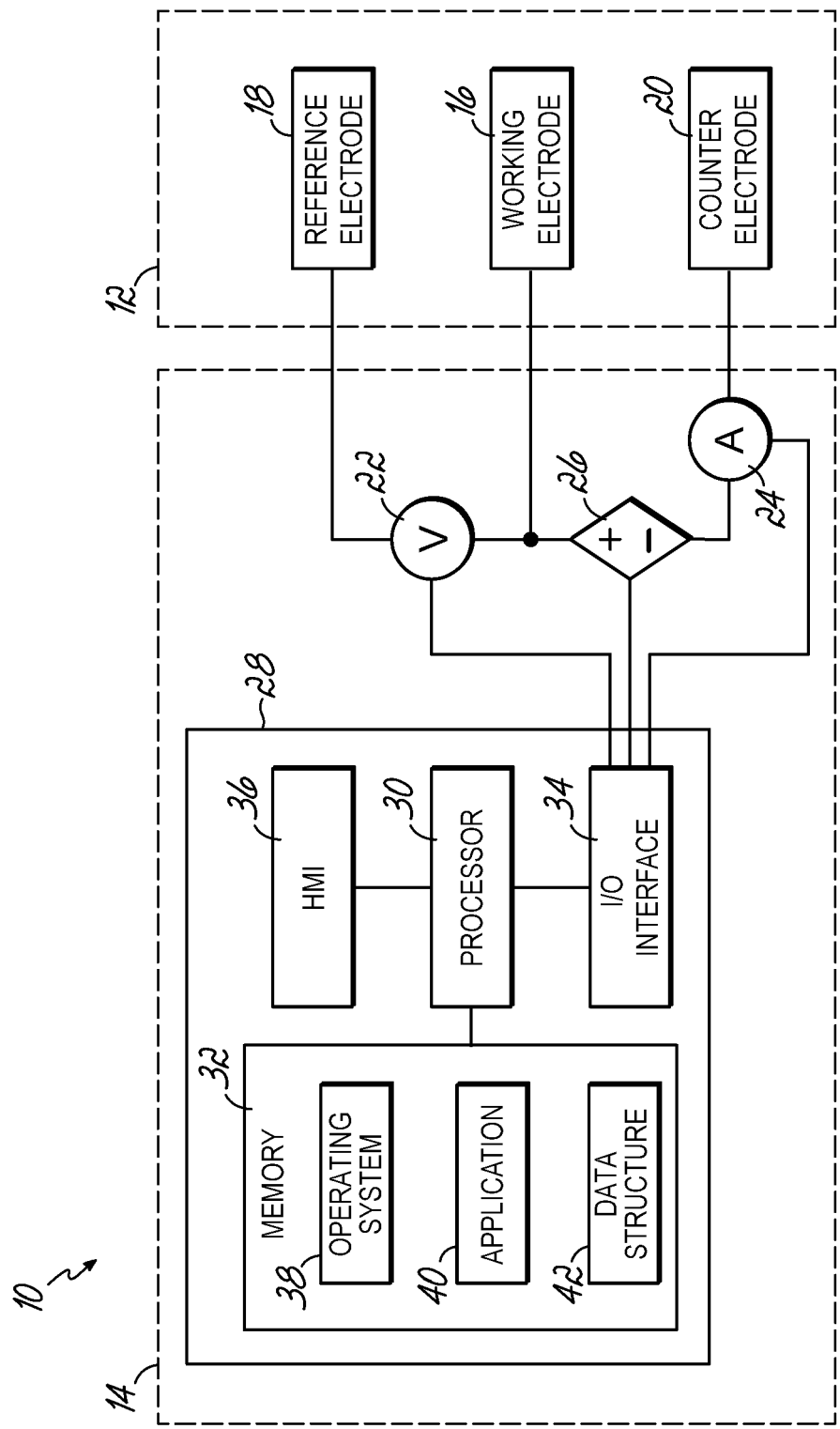
FIG. 1 is a schematic view of an exemplary sensing device in accordance with an embodiment of the invention.

As used herein, the term "about," when referring to a value or to an amount of mass, weight, time, volume, pH, size, concentration, or percentage, is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and operate the disclosed devices.

As used herein, the term "aptamer" means a molecule that undergoes a conformation change as an analyte binds to the molecule, and which satisfies the general operating principles of the sensing methods and devices as described herein. Such molecules include, e.g., natural or modified DNA, RNA, or XNA oligonucleotide sequences, spiegelmers, peptide aptamers, and affimers. Modifications may include substituting unnatural nucleic acid bases for natural bases within the aptamer sequence, replacing natural sequences with unnatural sequences, or other suitable modifications that improve sensor function. Typically, aptamers used in electrochemical sensors are tagged with a redox molecule such as methylene blue.

The devices and methods described herein encompass the use of sensors. A sensor, as used herein, is a device that is capable of measuring the concentration of a target analyte in solution. As used herein, an "analyte" may be any inorganic or organic molecule, for example: a small molecule drug, a metabolite, a hormone, a peptide, a protein, a carbohydrate, a nucleic acid, or any other composition of matter. The target analyte may comprise a drug. The drug may be of any type, for example, including drugs for the treatment of the cardiac system, the treatment of the central nervous system, that modulate the immune system, that modulate the endocrine system, an antibiotic agent, a chemotherapeutic drug, or an illicit drug. The target analyte may comprise a naturally-occurring factor, for example a hormone, metabolite, growth factor, neurotransmitter, etc. The target analyte may comprise any other species of interest, for example, species such as pathogens (including pathogen induced or derived factors), nutrients, and pollutants, etc.

As used herein, the term "continuous sensing" may be satisfied by a device recording a plurality of readings over a period of time during which the sensing occurs. Thus, even a point-of-care testing device which provides a single data point can be considered a continuous sensing device if, for example, the test has a 15 minute duration, and the testing device operates by taking multiple data points over 15 minutes and averaging them to provide a single data measure.

As used herein, the term "electrode" may apply to any material that is electrically conductive such as gold, platinum, nickel, silicon, conductive liquid infused materials such as ionic liquids, PEDOT:PSS, conductive oxides, carbon, boron-doped diamond, nanotubes or nanowire meshes, or other suitable electrically conducting materials.

As used herein, the term "redox tag" or "redox molecule" means any species such as small or large molecules with a redox active portion that, when brought adjacent to an electrode, can reversibly transfer at least one electron with the electrode. Redox tag or molecule examples include, but are not limited to, methylene blue, ferrocene, quinones, or other suitable species that satisfy the definition of a redox tag or molecule. In some cases, a redox tag or molecule is referred to as a redox mediator. Redox tags or molecules may also exchange electrons with other redox tags or molecules.

As used herein, the term "analyte" means any solute in a solution or fluid which can be measured using a sensor. Analytes can be small molecules, proteins, peptides, electrolytes, acids, bases, antibodies, molecules with small molecules bound to them, DNA, RNA, drugs, chemicals, pollutants, or other solutes in a solution or fluid.

As used herein, the term "sample fluid" means any solution or fluid that may contain at least one analyte to be measured.

As used herein, the midpoint voltage of a scan range is an average of the minimum and maximum voltages of the scan range.

DETAILED DESCRIPTION OF THE INVENTION

One or more specific embodiments of the present invention are described below. In an effort to provide a concise description of these embodiments, all features of an actual implementation may not necessarily be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Certain embodiments of the present invention show sensors as simple individual elements. It is understood that many sensors require two or more electrodes, reference electrodes, or additional supporting technology or features that, for purposes of clarity, are not necessarily described herein. Sensors may measure one or more characteristics of an analyte. Sensors are typically electrical in nature, but may also include optical, chemical, mechanical, or other known sensing mechanisms. Sensors can be in duplicate, triplicate, or more, to provide improved data and readings. Sensors may provide continuous or discrete data and/or readings. Certain embodiments of the present invention may show certain sub-components of sensing devices, but may omit additional sub-components inherent in the device in various applications that are known, e.g., a battery, antenna, or adhesive. These omissions may be for purposes of brevity, and to focus on certain inventive aspects of the disclosed embodiments of the present invention. All ranges of parameters disclosed herein include the endpoints of the ranges.

FIG. 1 depicts an exemplary sensing device 10 in accordance with an embodiment of the present invention that includes a sensor 12 and a detection circuit 14. The sensor 12 may include one or more electrodes, e.g., a working electrode 16, a reference electrode 18, and a counter electrode 20. The working electrode 16 may include a sensing portion and a conductive portion. The sensing portion may be affinity-based, and may include, for example, one or more redox-tagged aptamers. The aptamers may be selective in reversible binding to an analyte, thiol bonded to the conductive portion, and used to sense an analyte by means of electrochemical detection. The conductive portion of working electrode 16 may include a suitable conductive material, such as gold, carbon, or other suitable electrically conducting material. The aptamers of the sensing portion of working electrode 16 that are not bound to their target molecule may position their redox tags at an unbound distance from the conductive portion of the working electrode 16. In response to binding with a target molecule, each aptamer may change shape, thereby moving its redox tag closer to (or further away from) the conductive portion of working electrode 16. This change in distance may produce a corresponding change in the ability of the redox tag to transfer electrical charge between the working electrode 16 and a sample fluid. Thus, the sensing device 10 may be electrical in nature, and may utilize an attached redox couple to transduce an electrochemical signal, e.g., by increasing or decreasing the resistance of the sensor 12 to faradaic currents in response to changes in the concentration of target molecules in the sample fluid.

The detection circuit 14 may include a voltage sensor 22, a current sensor 24, a voltage source 26, and a controller 28. The voltage sensor 22 may be operatively coupled to the working and reference electrodes 16, 18 to measure a voltage therebetween. The current sensor 24 may be operatively coupled to the working and counter electrodes 16, 20 to measure a current flowing therebetween. The voltage source 26 may be operatively coupled to the working and counter electrodes 16, 20, and may be controlled by the controller 28 to selectively apply voltages between the working and counter electrodes 16, 20. In an alternative embodiment of the invention, the reference electrode 18 may be omitted, in which case the voltage sensor 22 may be configured to measure the voltage between the working and counter electrodes 16, 20.

The controller 28 may comprise a computing device that includes a processor 30, a memory 32, an input/output (I/O) interface 34, and a Human Machine Interface (HMI) 36. The processor 30 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions stored in memory 32. Memory 32 may include a single memory device or a plurality of memory devices including, but not limited to, read-only memory (ROM), random access memory (RAM), volatile memory, non-volatile memory, static random access memory (SRAM), dynamic random access memory (DRAM), flash memory, cache memory, or data storage devices such as a hard drive, optical drive, tape drive, volatile or non-volatile solid state device, or any other device capable of storing data.

The processor 30 may operate under the control of an operating system 38 that resides in memory 32. The operating system 38 may manage computer resources so that computer program code embodied as one or more computer software applications 40 residing in memory 32 can have instructions executed by the processor 30. One or more data structures 42 may also reside in memory 32, and may be used by the processor 30, operating system 38, or application 40 to store or manipulate data.

The I/O interface 34 may provide a machine interface that operatively couples the processor 30 to other devices and systems, such as the voltage sensor 22, current sensor 24, and voltage source 26. The application 40 may thereby work cooperatively with the other devices and systems by communicating via the I/O interface 34 to provide the various features, functions, applications, processes, or modules comprising embodiments of the invention.

The HMI 36 may be operatively coupled to the processor 30 of controller 28 to allow a user to interact directly with the sensing device 10. The HMI 36 may include video or alphanumeric displays, a touch screen, a speaker, and any other suitable audio and visual indicators capable of providing data to the user. The HMI 36 may also include input devices and controls such as an alphanumeric keyboard, a pointing device, keypads, pushbuttons, control knobs, microphones, etc., capable of accepting commands or input from the user and transmitting the entered input to the processor 30.

Figure 2:
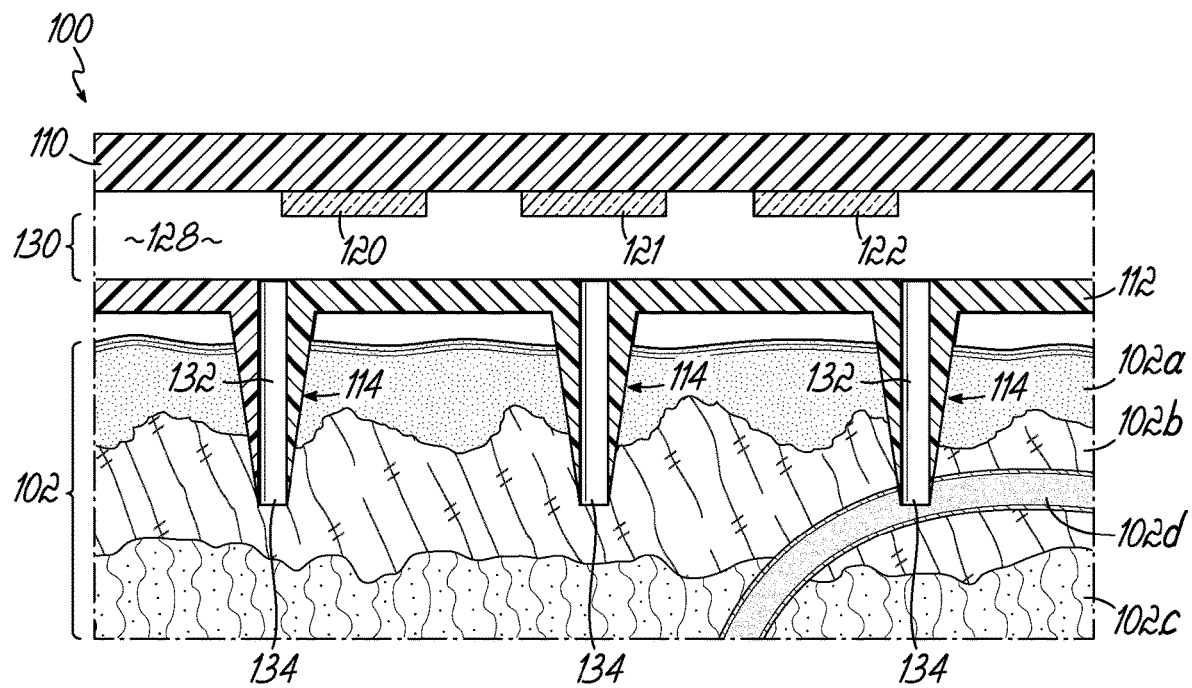
FIGS. 2-5 are cross-sectional schematic views of additional exemplary sensing devices in accordance with embodiments of the invention.

With reference to FIG. 2, in an embodiment of the present invention, an exemplary sensing device 100 is depicted as being placed partially in-vivo into a subject's skin 102, which includes an epidermis 102a, dermis 102b, and subcutaneous or hypodermis 102c. The sensing device 100 includes a non-conductive substrate 110 (e.g., a polymer), a microneedle assembly 112, and one or more electrodes 120-122 operatively coupled to the substrate 110. A portion of the sensing device 100 receives a fluid, e.g., an invasive biofluid such as interstitial fluid from the dermis 102b and/or blood from a capillary 102d. Access to the fluid may be provided, for example, by the microneedle assembly 112. The microneedle assembly 112 may be formed of metal, polymer, semiconductor, glass, or other suitable material, and include a plurality of microneedles 114. Each microneedle may include a lumen 132 having an inlet 134 that provides access to the fluid.

The exemplary sensing device 100 further includes a sample volume 128 comprising a space 130 defined between the microneedle assembly 112 and the substrate 110 and the lumens 132. The sample volume 128 may be filled with a microfluidic component such as capillary channels, a hydrogel, or other suitable material that operatively couples the fluid to the electrodes 120-122. Thus, a diffusion and/or advective flow pathway may be provided between the fluid and the electrodes 120-122. This pathway may begin at the inlets 134 to the microneedles 114 and reach the electrodes 120-122. Alternative arrangements and materials may also be possible, such as using a single needle, hydrogel polymer microneedles, or other suitable means to couple the fluid to the one or more electrodes 120-122. Thus, embodiments of the present invention are not limited to the depicted sensing device 100. In addition, a portion of sensing device 100, or even the entire sensing device 100, could be implanted into the body and perform similarly as described herein. For example, the electrodes 120-122 may be implanted inside the body on the end of an indwelling needle like those used in continuous glucose monitors.

The electrodes 120-122 may comprise or be part of an affinity-based electrochemical aptamer sensor that has a redox tag such as methylene blue. At least one of the electrodes 120-122 may be a working electrode functionalized with an aptamer. The aptamer may be selective in reversible binding to an analyte, thiol bonded to the conductive portion of the working electrode, and used to sense an analyte by means of electrochemical detection. One or more of the other electrodes 120-122 may comprise a counter electrode and/or a reference electrode.

The sensing device 100 of FIG. 2 is exemplary only for microneedle access of interstitial fluid, and it should be understood that the principles of the present invention may apply to any application of aptamer sensors such as monitoring for environmental pollutants, for food processing safety, for implanted sensors, or for other applications and devices.

Figure 3:
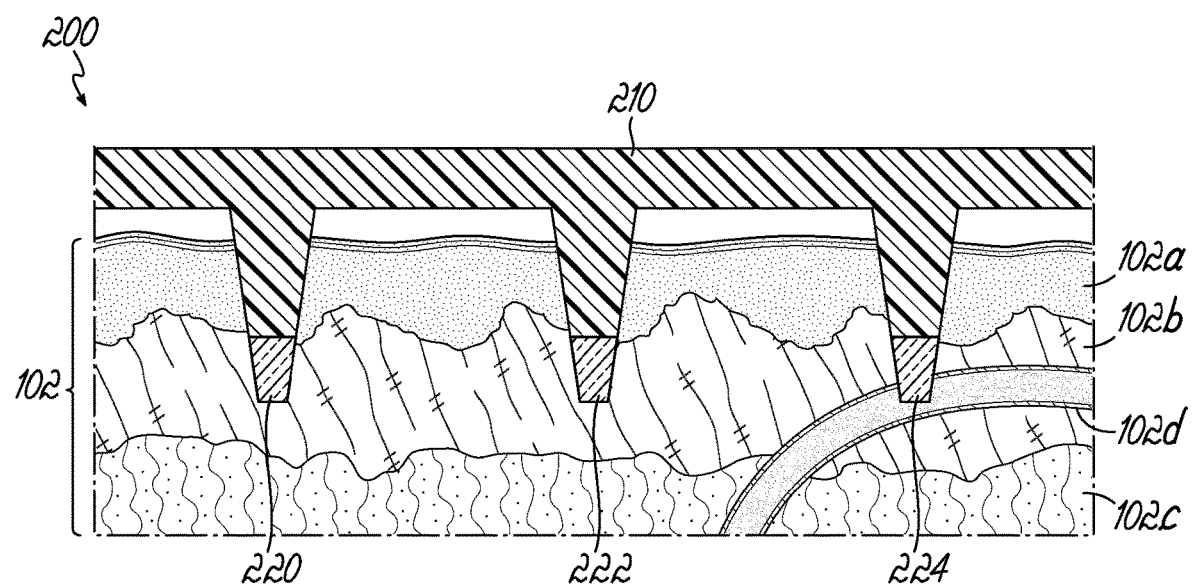
Figure 4:
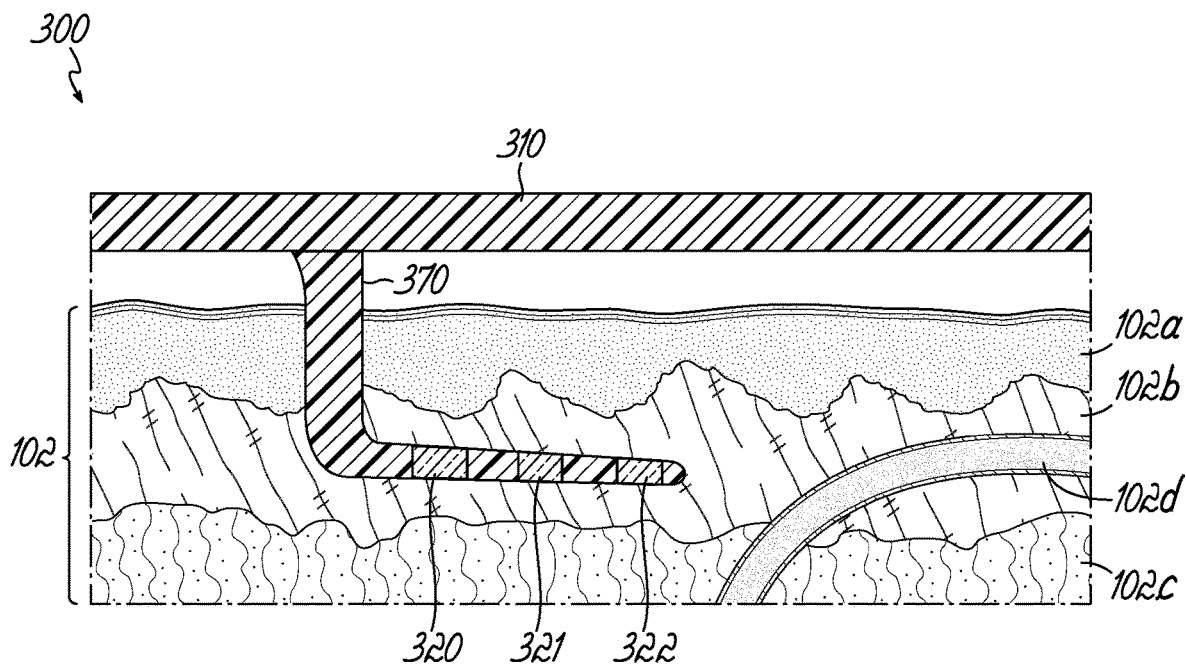
Figure 5:
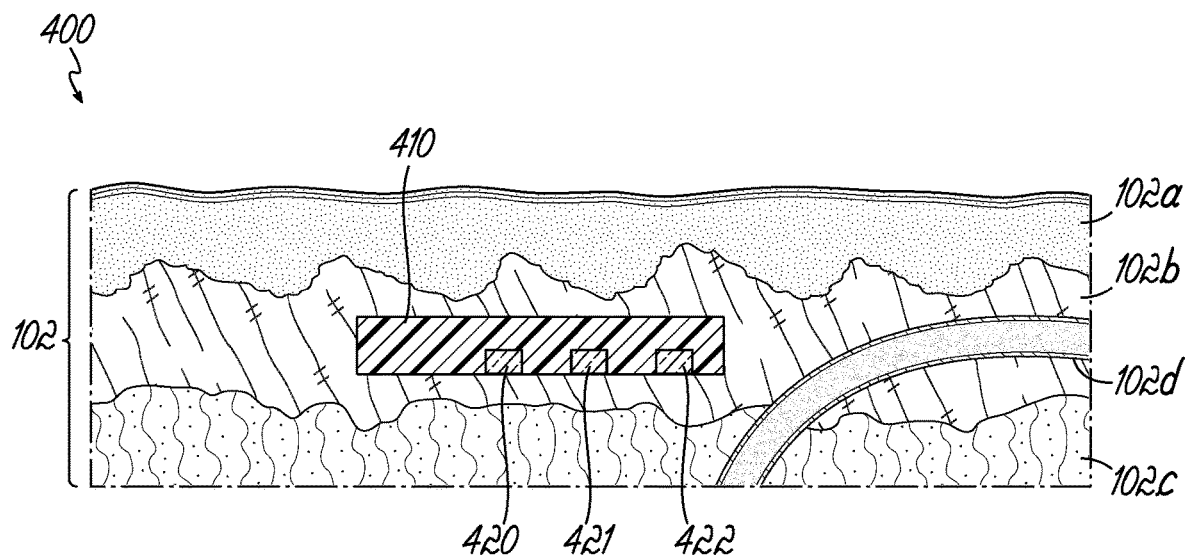

With reference to FIGS. 3-5, where like numerals refer to like features of the previous figures, FIG. 3 depicts an exemplary sensing device 200 in accordance with an alternative embodiment of the present invention that includes a substrate 210 and one or more electrodes 220-222. The electrodes 220-222 may be coupled to the substrate 210 and located in the dermis 102b so that they are in contact with a sample fluid. FIGS. 4 and 5 depict additional exemplary sensing devices 300, 400 in accordance with alternative embodiments of the present invention. Sensing device 300 includes a substrate 310 and a needle 370 having a plurality of electrodes 320-322. In use, the needle 370 may be inserted through the epidermis 102a so that a distal end of the needle 370 extends into the dermis 102b. The electrodes 320-322 may be located at the distal end of the needle 370 so that they are exposed to fluids in the dermis 102b. In FIG. 4, the sensing device 410 may be implanted in the skin 102 or some other location in the body. The sensing device 410 includes one or more electrodes 420-422 that may be in contact with fluids so as to detect the presence of a one or more analytes at the implantation site.

In operation, an input signal may be applied to one or more of the electrodes (e.g., a voltage may be applied across the working electrode and the counting electrode), and one or more electrical signals measured (e.g., a voltage between the working and reference electrodes, and a current flowing between the working and counter electrodes) while the input signal is applied. The response of the sensor to the input signal may then be determined. For example, a sensor response may be generated by plotting the current flowing between the working and counter electrodes as a function of the voltage measured across the working and reference electrodes. How efficiently the redox tag transfers electrical charge between the working electrode and sample fluid may depend in part on the characteristics of the input signal. Peak charge transfer efficiency may occur, for example, at one or more of a particular input voltage, current, frequency, or scan rate. As a result, the sensor response (e.g., a plot of current verses voltage) may include a redox peak corresponding to the input signal at which this peak charge transfer efficiency occurs. This redox peak may coincide with a peak electron transfer rate $k_{ET}$ of the working electrode, and may be analyzed to determine an amount of the total current that is due to the redox tags transferring charge between the working electrode and fluid sample. Thus, one or more characteristics of the redox peak (e.g., height, width, area, etc.) may provide an indication of the amount of the target molecule in the sample fluid.

Figure 6A:
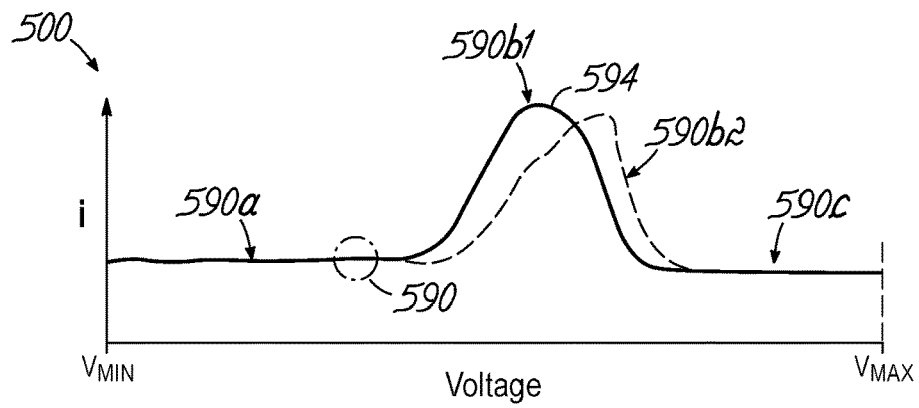
FIGS. 6A-6C are graphical views illustrating sampling methods and ways of defining peak and baseline regions of a voltage scan.

FIG. 6A depicts a graph 500 that includes a plot 590 of current versus voltage representing an exemplary response of the sensing device 10 to application of an input signal to the sensor 12. In a typical operational environment, the input signal may be a swept voltage with a $V_{MIN}$ of about 0 volts and a $V_{MAX}$ of about −0.4 volts. Aptamers with redox tags on working electrodes are typically measured using a form of pulse voltammetry, such as Square Wave Voltammetry (SWV), although other methods may also be used. In SWV, an input signal in the form of a voltage (V) is swept, and causes a corresponding output signal in the form of a current output (i). As described above, at least a portion of this current may result due to the redox tag transferring electrical charge to or from the working electrode.

Whether SWV or another method is used to scan the sensor, a voltage scan range is typically used that provides a "full scan". A full scan normally includes a baseline region 590a, 590c having a baseline current, and at least one redox peak region 590b1 having a redox peak 594. Measuring the baseline current generated in the baseline region 590a, 590c may improve accuracy as the magnitude of the current in the peak region 590b1, 590b2 can shift over time as the baseline current in the baseline region 590a, 590c increases or decreases. This shift in magnitude may be due to fouling, loss of the blocking layer, or other factors. Furthermore, the position of the redox peak 594 in the voltage scan can also shift over time (e.g., to peak region 590b2) due to effects such as changes in pH, fouling, analyte binding, salinity, reference electrode degradation, and other factors. In cases where the potential of the working electrode is measured relative to that of another electrode (e.g., the reference or counter electrode), changes in the potential of that electrode may also shift the position of the redox peak 594.

Methods other than SWV may also be used to stimulate the sensor 12, e.g., amperometric methods, etc. However, because in all cases the electron transfer to or from a redox tag is measured, a sufficient voltage must be applied to induce that electron transfer. The voltage that must be applied to cause electron transfer to or from the redox tag can drift significantly due to several reasons. These reasons may include changes in biofluid or sample fluid composition, and fouling of any of the sensor electrodes. In some cases, the required voltage can shift by as much as hundreds of millivolts for electrodes placed in solution, and is not always avoidable, even with use of a sealed reference electrode.

Figure 6B:
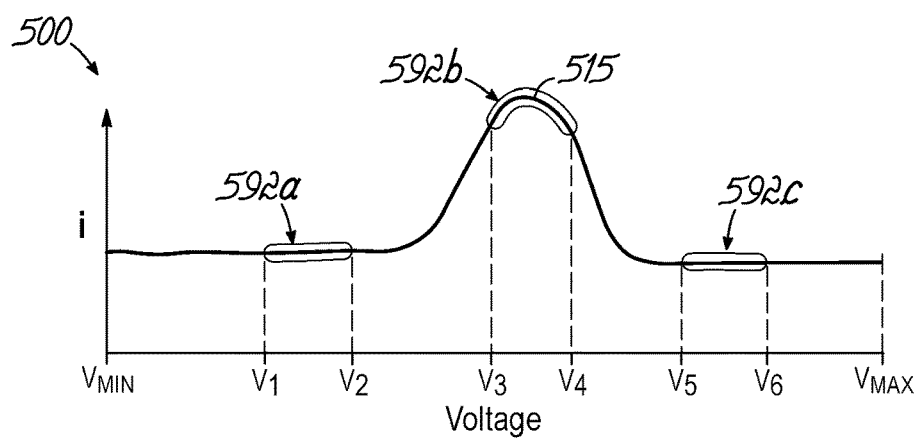

As illustrated in FIG. 6A, the above described voltage shift may result in the redox peak 594 moving to a new position, e.g., from peak region 590b1 to peak region 590b2. Although the exemplary peak shift depicted has a positive voltage shift, it should be understood that a negative voltage shift can occur as well. In order to track the peak position, and therefore the reference potential, the full scan 590 may be measured as illustrated in FIG. 6A. In an alternative embodiment, partial scans 592a, 592b, 592c may be performed that only cover certain voltage ranges in the baseband and peak regions of the full scan, as illustrated in FIG. 6B. Advantageously, by reducing the duty cycle of the scan as compared to a full scan, partial scans may reduce degradation of the electrodes and extend the life of the sensor.

The peak position may be tracked based on the slope (e.g., di/dv) of the current/voltage function of the sensor. For example, a zero derivative (slope) measurement of the current vs. voltage scan in the peak region 590b1, 590b2 of scan 590 may provide an indication of the peak position. Thus, the position of the redox peak 594 may be determined by detecting an increasing slope, followed by a zero slope, followed by a decreasing slope, with the redox peak being located in the zero slope region. Other ways of determining the position of the redox peak may include fitting a curve (e.g., a polynomial curve) to the scan data, and determining the position of the redox peak in the fitted curve. Software and/or electronics may be used to track the peak position on a voltammogram similar to that shown in FIGS. 6A and 6B.

The partial scan depicted by FIG. 6B includes portions of the voltage scan range which produce a plurality of current baseline sample ranges 592a, 592c (e.g., two current sample ranges associated with scanning voltage sub-ranges $V_1$-$V_2$ and $V_5$-$V_6$, respectively) and a current peak sample range 592b ($V_3$-$V_4$). Measurements may also be made using only two of these portions of the full scan, e.g., one current baseline sample range 592a and the current peak sample range 592b. A partial scan may include also only one current sample range (e.g., a range that covers the peak sample range 592b and a portion of the baseline region on one or both sides of the peak sample range 592b), or any number of current sample ranges so long as the scan voltage sub-ranges used to generate the current sample ranges do not collectively comprise the full voltage scan range.

FIGS. 6A and 6B may represent a forward voltammogram scan, a backward voltammogram scan, a net voltammogram scan, a portion of a cyclic voltammogram, or some other scan, with one illustrative point of FIGS. 6A and 6B being that there exists a redox peak region and a baseline region, and that both provide information useful for evaluating signals from an aptamer based sensor. If the redox peak 594 drifts from peak region 590b1 to peak region 590b2, a peak partial scan may become misaligned with the peak region. Redox peak drift may also cause the redox peak to enter a baseline partial scan. In either case, redox peak drift may cause partial scans to become inaccurate. Therefore, the position of peak partial scans (e.g., starting and ending voltages) may benefit from tracking the position of the peaks 594b1, 594b2 over time. This is also true for a chronoamperometric scan, so that the correct voltage is applied during the chronoamperometric scan for maximum measurement accuracy and in some cases for minimum device degradation.

Figure 6C:
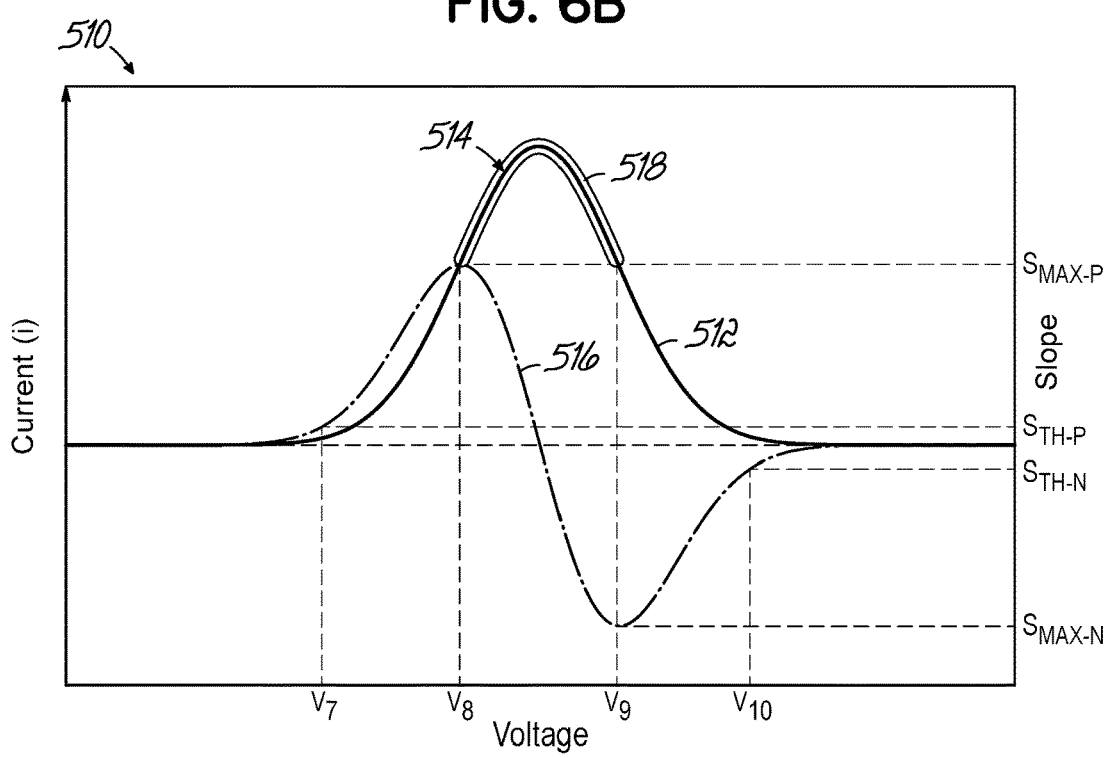

As an example of how the positions of peak and baseline regions of a scan suitable for determining a peak or baseline current may be determined based on the slope of the current/voltage function, FIG. 6C depicts a graph 510 including an exemplary plot 512 of a voltage scan with a peak region 514 having a peak 515, and a plot 516 showing the slope (di/dv) of the voltage scan. The slope of the voltage scan may have a peak positive slope $S_{MAX-P}$ at voltage $V_8$, and a peak negative slope $S_{MAX-N}$ at voltage $V_9$. A peak sample range 518 may be defined, for example, as a portion of the peak region 514 between the peak positive slope $S_{MAX-P}$ and the peak negative slope $S_{MAX-N}$. In an alternative embodiment, the peak sample range 518 may be defined as a percentage of the voltage range $V_8$-$V_9$ defined by the peak positive and negative slopes $S_{MAX-P}$, $S_{MAX-N}$, e.g., as 75%, 50%, 20%, 10%, 5%, 2%, or 1% of the voltage range $V_8$-$V_9$. In another alternative embodiment, the peak sample range 518 may be defined as a portion of the voltage scan between a voltage $V_7$ at which the scan slope exceeds a positive slope threshold $S_{TH-P}$, and a voltage $V_{10}$ at which the scan slope exceeds a negative slope threshold $S_{TH-N}$. Each of the positive and negative slope thresholds $S_{TH-P}$, $S_{TH-N}$ may be defined, for example, as a percentage of the peak positive slope $S_{MAX-P}$ and/or peak negative slope $S_{MAX-N}$, e.g., 75%, 50%, 20%, 10%, 5%, 2%, or 1% of the peak positive or peak negative slopes $S_{TH-P}$, $S_{TH-N}$. The edges of the peak region 214 may also be defined based on the slope of the voltage scan passing through one or more slope thresholds, and the peak position may be defined as the scan voltage at which the slope of the voltage scan passes through zero between the peak positive and peak negative slopes $S_{MAX-P}$, $S_{MAX-N}$. In an alternative embodiment, the edges of the peak region 214 may be defined as being a predetermined voltage below the positive slope threshold $S_{TH-P}$ and at a predetermined voltage above the negative slope threshold $S_{TH-N}$. In yet another embodiment, the peak edges and position may be defined by voltages at which the current i of the voltage scan exceeds one or more thresholds.

Using these methods, the required applied voltage between a working electrode and counter electrode can be measured in real time and made more accurate when voltage is applied regardless of reference voltage drift. Depending on signal quality, the redox peak position may be determined within less than 200 mV, 100 mV, 50 mV, 20 mV, 10 mV, 5 mV, or even less than 1 mV of its actual voltage position. After the peak position is determined, then a full scan or partial scan may be performed with the corrected voltage(s). Likewise, the applied voltage for another technique such as chronoamperometry can be adjusted as well. Without accurately knowing the correct peak position and proper applied voltage, one could also simply provide an overvoltage, i.e., scan to greater voltages, or chronoamperometric pulse at a higher voltage. However, providing an overvoltage may increase background current and cause degradation of the sensor. Therefore, the applied voltage may be controlled such that it does not exceed the magnitude of the redox peak of the redox tag by more than a value selected from the group consisting of 1 mV, 10 mV, 50 mV, 200 mV, and 500 mV. As a result, embodiments of the present invention may utilize simpler reference and counter electrodes, and may also use those reference and counter electrodes with less concern about voltage drift.

Figure 7:
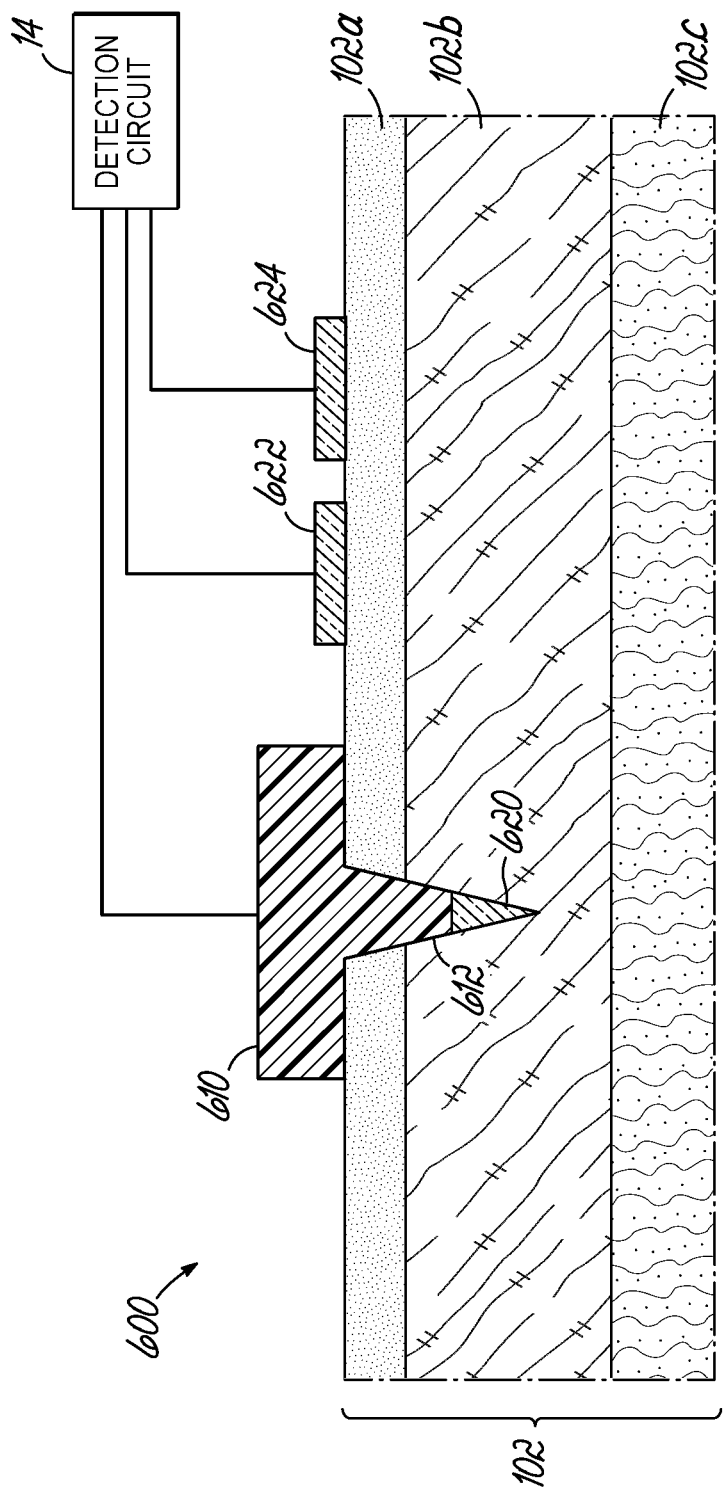
FIG. 7 is a cross-sectional schematic view of an additional exemplary sensing device in accordance with an embodiment of the invention.

FIG. 7 depicts an exemplary sensing device 600 that includes a detection circuit 14, a conductive substrate 610 having a projection 612 which extends into the dermis 102b of skin 102, a working electrode 620, and one or more of a reference electrode 622 and a counter electrode 624. The detection circuit 14 may be operatively coupled to the working electrode 620, and one or both of the reference electrode 622 and counter electrode 624. The working electrode 620 may be located on a distal end of the projection 612 so that the working electrode 620 is in contact with a dermal fluid. The reference electrode 620 and counter electrode 622 may be located externally to (e.g., on the surface of) the skin 102. Although depicted as separate electrodes, it should be understood that in an alternative embodiment, the sensing device 600 may have only one electrode that serves as both the reference and counter electrode.

Depending on the materials chosen for the electrodes 622, 624 (e.g., gel-adhesive, metal, other suitable electrode materials) as well as variabilities in contact/pressure between the electrodes 622, 624 and the skin 102, or other confounding factors, the reference potential may shift dramatically, e.g., by hundreds of mV or more. Therefore, the devices and methods described above with respect to FIGS. 6A-6C may also be employed to correct for this drift in reference potential. In addition, when using external electrodes, the impedance between the reference electrode and the body should be low enough so that the potential of the region of the body proximate to the working electrode 620 where aptamers and redox tags are measured is reliably dropped.

That is, the potential of this region should not vary greatly due to contact and impedance of the external electrodes 622, 624 with skin 102.

For example, a dry gold electrode having an area of 0.5 cm$^2$ exposed to a 1 V peak-to-peak sinusoid (0.5V) may have a real impedance of about 10 k$\Omega$, and thus conduct a 0.5 V/10 k$\Omega$=50 $\mu$A current. In this example, the working electrode 620 could rely on 5 nA of current generation due to electron transfer from the redox tag plus background current. Therefore, the potential at the working electrode 620 would be as good as or better than if a reference electrode 622 or counter electrode 624 were placed in the body. By scaling the electrode area, location, contact material, wet vs. dry electrodes, or other features of the non-working electrodes to maintain the real impedance below a maximum allowable impedance, the voltage drop at the working electrode 620 may be maintained at >20%, >50%, or >90% of the total applied voltage.

The reference electrode need not be outside the body or out of direct contact with a biofluid, and yet the potential used at the working electrode 620 may still need to be determined using one or embodiments of the present invention, because the reference potential may not be fully stable. For example, a reference electrode could be a pseudo-reference electrode, such as gold, which is placed along with the working and counter electrodes in interstitial fluid. A pseudo-reference electrode, or other imperfect reference electrodes, can similarly benefit from the present invention regardless of location of those electrodes on or in the body.

In any case, it should be understood that embodiments of the invention are not limited to sensing fluids as shown in the exemplary embodiment described above, and may apply broadly to any sensing device that employs aptamers with a redox tag, including variations where the aptamers are in solution phase and held adjacent to the working electrode by a size-selective membrane (not shown). Such aptamers can also give a signal change, for example by undergoing a shape conformation change with analyte binding that changes availability of the redox tag to the electrode (measured by square wave voltammetry), changes diffusion coefficient of the aptamer (measured by amperometry), or other suitable technique in solution.

In general, the routines executed to implement the embodiments of the invention, whether implemented as part of an operating system or a specific application, component, program, object, module or sequence of instructions, or a subset thereof, may be referred to herein as "program code." Program code typically comprises computer-readable instructions that are resident at various times in various memory and storage devices (e.g., non-transitory storage media) in a computer and that, when read and executed by one or more processors in a computer, cause that computer to perform the operations necessary to execute operations or elements embodying the various aspects of the embodiments of the invention. Computer-readable program instructions for carrying out operations of the embodiments of the invention may be, for example, assembly language, source code, or object code written in any combination of one or more programming languages.

The terminology used herein is for the purpose of describing particular embodiments only and is not intended to be limiting of the embodiments of the invention. As used herein, the singular forms "a", "an" and "the" are intended to include both the singular and plural forms, and the terms "and" and "or" are each intended to include both alternative and conjunctive combinations, unless the context clearly indicates otherwise. It will be further understood that the terms "comprises" or "comprising," when used in this specification, specify the presence of stated features, integers, actions, steps, operations, elements, or components, but do not preclude the presence or addition of one or more other features, integers, actions, steps, operations, elements, components, or groups thereof. Furthermore, to the extent that the terms "includes", "having", "has", "with", "comprised of", or variants thereof are used in either the detailed description or the claims, such terms are intended to be inclusive in a manner similar to the term "comprising".

While all the invention has been illustrated by a description of various embodiments, and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. A sensing device for measuring an analyte, the device comprising:
    a sensor including a plurality of electrodes including a working electrode and a counter electrode, the working electrode including a plurality of molecules that reversibly bind to the analyte, and an attached redox tag; and
    a detection circuit operatively coupled to the sensor and configured to:
        apply a first scan to the sensor, the first scan having a first scan range,
        determine a position of a redox peak in the first scan,
        apply a second scan to the sensor, the second scan having a second scan range,
        determine a shift in the position of the redox peak in the second scan relative to the first scan,
        in response to determining the shift in the position of the redox peak, define a third scan range that is more closely aligned with the shifted position of the redox peak than the first scan range, and
        apply a third scan having the third scan range to the sensor.

2. The device of claim 1, wherein the detection circuit is further configured to:
    determine, based on the second scan, a measured scan voltage at which a measured current at least a portion of which is due to an electron transfer rate of the redox tag is at a peak value.

3. The device of claim 2, wherein the measured scan voltage is within 200 mV, 100 mV, 50 mV, 20 mV, 10 mV, 5 mV, or 1 mV of a working electrode voltage at which the measured current is at the peak value.

4. The device of claim 2, wherein the measured scan voltage is used to determine the third scan range, and a midpoint voltage of the third scan range is no more than 200 mV, 100 mV, 50 mV, 20 mV, 10 mV, 5 mV, or 1 mV different than the measured scan voltage.

5. The device of claim 1, wherein at least one of the plurality of electrodes is configured to be external to a body without direct contact with a biofluid in the body and is in conductance with the working electrode, and the working electrode is in electrical contact with the biofluid originating in the body.

6. The device of claim 5, wherein the at least one of the plurality of electrodes configured to be external to the body is a reference electrode.

7. The device of claim 5, wherein the at least one of the plurality of electrodes configured to be external to the body is the counter electrode.

8. The device of claim 1, wherein a voltage drop at the working electrode is at least one of >20%, >50%, or >90% of a total applied voltage between the working electrode and the counter electrode.

9. The device of claim 1, wherein
the plurality of electrodes further includes at least one non-working electrode configured to be applied externally to a body without direct contact with a biofluid in the body such that the non-working electrode is in conductance with the working electrode when the working electrode is in electrical contact with the biofluid originating in the body.

10. The device of claim 9, wherein the at least one non-working electrode is a reference electrode.

11. The device of claim 9, wherein the at least one non-working electrode is the counter electrode.

12. The device of claim 9, wherein the voltage drop at the working electrode is >20%, >50%, or >90% of a total applied voltage between the working electrode and the non-working electrode.

13. The device of claim 1, wherein the plurality of molecules that reversibly bind to the analyte are aptamers.

14. The device of claim 1, wherein the first scan range and the second scan range have the same minimum and maximum values.

15. A method for measuring an analyte with a device comprising a sensor and a detection circuit, comprising:
applying a first scan to the sensor, the first scan having a first scan range,
determining a position of a redox peak in the first scan,
applying a second scan to the sensor, the second scan having a second scan range,
determining a shift in the position of the redox peak in the second scan relative to the first scan,
in response to determining the shift in the position of the redox peak, defining a third scan range that is more closely aligned with the shifted position of the redox peak than the first scan range, and
applying a third scan having the third scan range to the sensor.

16. The method of claim 15, wherein the first scan includes one or more portions of a voltage range associated with a full scan.

17. The method of claim 16, wherein the one or more portions of the voltage range associated with the first scan includes a baseline scan.

18. The method of claim 15, further comprising:
determining, based on the second scan, a measured scan voltage at which a measured current at least a portion of which is due to an electron transfer rate of a redox tag is at a peak value.

19. The method of claim 18, wherein the measured scan voltage is within 200 mV, 100 mV, 50 mV, 20 mV, 10 mV, 5 mV, or 1 mV of a working electrode voltage at which the measured current is at the peak value.

20. The method of claim 18, wherein the measured scan voltage is used to determine the third scan range, and a midpoint voltage of the third scan range is no more than 200 mV, 100 mV, 50 mV, 20 mV, 10 mV, 5 mV, or 1 mV different than the measured scan voltage.

* * * * *